United States Patent [19]

Takashio et al.

[11] Patent Number: 4,882,280

[45] Date of Patent: Nov. 21, 1989

[54] URICASE AND A METHOD FOR THE PREPARATION THEREOF

[75] Inventors: Masachika Takashio, Yaizu; Takahide Chikano, Shizuoka; Minoru Kamimura, Yaizu, all of Japan

[73] Assignee: Sapporo Breweries Limited, Tokyo, Japan

[21] Appl. No.: 866,572

[22] Filed: May 22, 1986

[30] Foreign Application Priority Data

Jun. 5, 1985 [JP] Japan ................................. 60-120399

[51] Int. Cl.[4] .......................... C12N 1/20; C12N 9/80; C12N 9/06; C12N 1/22; C12R 1/07; C12Q 1/62

[52] U.S. Cl. ................................ 435/228; 435/253.6; 435/832; 435/10; 435/191; 435/252.5

[58] Field of Search ........................... 435/10, 191, 832

[56] References Cited

U.S. PATENT DOCUMENTS 3,810,820  5/1974  Laboureur et al. ................. 435/191

4,753,882  5/1988  Takashio et al. ................... 435/228

OTHER PUBLICATIONS

Mahler, J. L., Analytical Biochemistry, vol. 38, pp. 65–84, (1970).

Primary Examiner—Thomas G. Wiseman
Assistant Examiner—Joan Ellis
Attorney, Agent, or Firm—Frishauf, Holtz, Goodman & Woodward

[57] ABSTRACT

Different from conventional uricase products, the uricase of the present invention has outstandingly high thermal stability and is active in a wide range of pH from 5 to 10 for the oxidative decomposition of uric acid undertaken in clinical analysis. The uricase of the invention is produced microbiologically by a thermophilic microorganism belonging to the genus of Bacillus and especially named as *Bacillus sp.* TB-90 which is a novel species distinguishable from any of the microorganisms belonging to the genus of Bacillus.

1 Claim, 3 Drawing Sheets

URICASE AND A METHOD FOR THE PREPARATION THEREOF

BACKGROUND OF THE INVENTION

The present invention relates to a novel uricase and a method for the preparation thereof. Uricase is an enzyme useful as a reagent in the quantitative determination of uric acid and the present invention provides a novel uricase having properties quite suitable for this purpose, which can be produced by a thermophilic microorganism.

Uricase (EC 1.7.3.3) is an enzyme found in the livers and kidneys of animals as well as certain microorganisms and catalyses the oxidation of uric acid in the presence of oxygen so that it is used widely in the quantitative determination of uric acid in clinical examinations.

As is disclosed in Japanese Patent Kokai Koho Nos. 55-81586 and 56-124381, Japanese Patent Publication No. 56-43230, uricase is widely produced by a microbiological means while one of the problems in these microbiological processes is that the culturing of the microorganism takes a considerably long time of one day to three days or even longer because the microorganism utilized in the process disclosed in each of the above mentioned patent literatures is mesophilic.

While it would be an advantageous way to utilize a thermophilic microorganism exhibiting a high rate of metabolism and capable of rapid growth in respect of the possibility of decreasing the time taken for the microbiological production of uricase, no such a process has yet been reported in which a thermophilic microorganism is utilized for the production of uricase. It would also be an advantageous way to utilize a thermophilic microorganism as a source of uricase in respect of the excellent stability of the produced enzyme.

As viewed from the standpoint of the activity characteristics of a uricase, it is desirable that the uricase should have a high activity in the pH range including or in the vicinity of pH 6.5 in order to reduce the amount of the enzyme required in the clinical analysis for uric acid because the common determination of uric acid is performed by the coupled reaction with peroxidase from horseradish which exhibits the optimum activity at a pH of about 6.5. Nevertheless, the uricases conventionally used in the prior art have an optimum pH in the range of 8.5 to 9.0 and can exhibit substantially no activity at a pH of 6.5 (see Japanese Patent Publication 56-43230) or the activity at a pH of 6.5 is lower than 40% of the activity at a pH of 8.5 to 9.0 [see Agric. Biol. Chem., volume 44(12), page 2811 (1980)].

In view of the above described problems in the prior art in connection with uricases, the inventors have conducted extensive searching works to discover a thermophilic microorganism capable of producing a uricase having activity in a wide pH range among the thermophilic microorganisms separated from a large number of soil samples and finally reached a discovery leading to the establishment of the present invention.

SUMMARY OF THE INVENTION

Thus, the present invention provides a novel uricase which has an activity for the oxidative decomposition of uric acid over a wide pH range from 5 to 10.

The above defined novel uricase of the invention is a microbiological product produced by a microorganism belonging to the genus of thermophilic Bacillus and named Bacillus sp. TB-90, referred to merely as TB-90 hereinbelow.

The method of the present invention for the preparation of the novel uricase accordingly comprises culturing the above mentioned microorganism TB-90 in a nutrient culture medium so that the microorganism produces the uricase and separating the accumulated uricase.

DETAILED DESCRIPTION OF THE PREFERRED EMBODIMENTS

Figure 1:
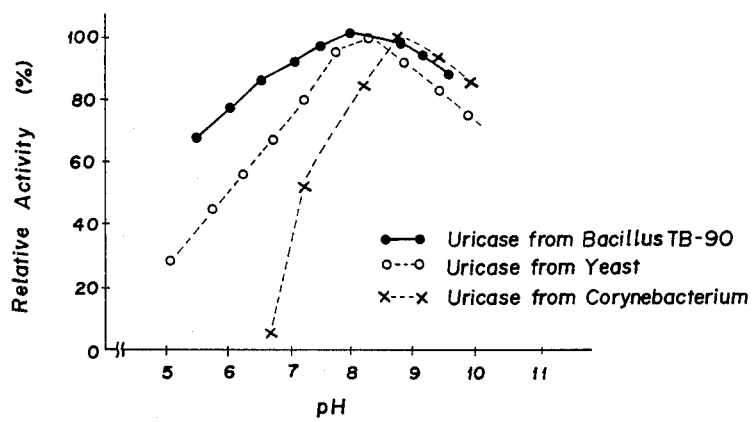
FIGS. 1, 2, 3, 4 and 5 each illustrate the optimum pH, the pH range of stability, the optimum temperature for the activity, the temperature range for stability and resistance against sodium dodecylsulfate, respectively, of the novel uricase of the present invention.

The microorganism used in the inventive method for the microbiological production of the novel uricase is not particularly limitative provided that it is a thermophilic microorganism belonging to the genus of Bacillus and capable of producing the above defined novel uricase. Such a microorganism includes not only the above mentioned TB-90 but also any natural or artificial mutant strains thereof as well as various kinds of organisms into which the genes of the above mentioned bacterial strains have been transferred provided that they have an ability of producing the novel uricase.

Following are the bacteriological properties by which the microorganism of TB-90 is characterized. The examination of these properties was carried out according to the procedure and using the formulation of the culture medium described in the books of "Classification and identification of microorganisms" edited by T. Hasegawa, published by Tokyo University Press and "Methods of identification of microorganisms" published by Eisei Gijutsu Kai, Japan.

[Morphological characteristics] (after 18 hours of culturing at 55° C.)

1. Shape and dimensions of cells: rods, 0.5–0.8 × 1.3–2 μm
2. Polymorphism: none
3. Motility: none
4. Spores: circular endogenous spores formed at the center of a cell
5. Gram reaction: positive
6. Acid-fast stain: none
7. Capsules: none
8. Metachromatic granule: none

[Cultural properties] (after 18 hours culturing at 55° C.)

1. Nutrient-agar plate culture
Shape: circular
Periphery: smooth
Elevation: flat
Luster: not strong
Surface: somewhat coarse
Color: translucent
2. Nutrient-agar slant culture
Growth: good
Shape: filamentous
3. Nutrient liquid culture
Surface growth: none
Turbidity: clear Precipitates: a little
Coloration and decoloration: none
4. Nutrient-gelatin stab culture (examination of the solidified
  state of the medium by cooling after culturing at 55° C. for a length of time, 30% gelatin added)
  good growth with a large volume of precipitates but no liquefaction of gelatin
5. Nutrient-agar stab culture
  Shape: torous (in the vicinity of surface only)
  Surface growth: good
6. Reaction on litmus milk
  no decoloration of litmus, pH unchanged, no coagulation, no liquefaction

[Physiological properties] (after 1–2 days of culturing at 55° C.)
1. Reduction of nitrates: none
2. MR test: negative
3. V-P test: negative
4. Formation of indole: no
5. Formation of hydrogen sulfide: no
6. Hydrolysis of starch: yes
7. Utilization of citric acid: no
8. Utilization of ammonium salt: yes
9. Formation of coloring matter: no
10. Oxidase activity: yes
11. Catalase activity: yes
12. pH for growth: 4.5 to 7.5 with an optimum pH of 5.0 to 6.5
13. Temperature for growth: 38° to 62° C. with an optimum growth temperature of 50° to 60° C.
14. Growth in anaerobic culture medium: no
15. Growth in Sabouraud dextrose-agar culture medium: good
16. Growth at 55° C. in a culture medium containing 0.02% sodium azide: no
17. Growth in 0.001% lysozyme (tested at 45° C.): no
18. Deamination of phenylalanine: no
19. Tolerance against sodium chloride: growth in 3% NaCl but no growth in 5% NaCl
20. Vitamin requirement: yes
21. Decomposition of tyrosine: no

[Utilization of carbon sources]
The microorganism grows with formation of acid by assimilating D-xylose, D-glucose, D-galactose, trehalose, cellobiose and glycerin.

The microorganism does not utilize or little utilizes arabinose, mannose, fructose, maltose, sucrose, lactose, D-sorbitol, D-mannitol, starch, 2-keto-gluconate, adonitol, xylytol, methyl-D-glucoside, N-acetyl-D-glucosamine, melezitose and raffinose.

As a result of the examination undertaken according to the method of classification described in Bergey's Manual of Determinative Bacteriology, 8th edition (1974) making reference to the above mentioned bacteriological properties of the microorganism, the subject microorganism of TB-90 was identified to belong to the genus of Bacillus. Although it may be a tentative conclusion derived from the comparison with known species belonging to the genus of Bacillus that the above described TB-90 can be either of *Bacillus stearothermophilus, Bacillus coagulans* and *Bacillus brevis* in respect of the temperature range for growth, this tentative conclusion is not supported due to the lack of motility in TB-90. Moreover, TB-90 can be differentiated from *Bacillus stearothermophilus* in respect of the ability of growth in a Sabouraud dextrose agar culture medium, from *Bacillus coagulans* in respect of the inability of growth in an anaerobic agar culture medium and in the presence of 0.02% of sodium azide and from *Bacillus brevis* in respect of the production of acid from xylose, no production of alkali in a V-P culture medium and inability of decomposing casein and tyrosine. In addition, uricase could not be produced when the culturing procedure described below was undertaken of the type strains including *Bacillus stearothermophilus* IAM 11001, 11002, 11003, 11004 and 12043, *Bacillus coagulans* IAM 1194 and *Bacillus brevis* IAM 1031 deposited at Institute of Applied Microbiology of Tokyo University.

As is understood from the above given description, it is a fair conclusion that TB-90 is a novel species belonging to the genus of Bacillus. Accordingly, a strain of TB-90 has been deposited at Fermentation Research Institute, Agency of Industrial Science and Technology, Japan, as FERM BP-795.

The uricase of the invention can be prepared by culturing the microorganism capable of producing the uricase in a culture medium to form the uricase and separating said uricase.

The nutrient culture medium used in the inventive method is not particularly limitative including natural and synthetic components containing a carbon source, a nitrogen source, inorganic materials and, according to need, growth factors required by the microorganism in a well-balanced proportion.

The carbon source suitable for use includes glucose, xylose, galactose, glycerin and other carbohydrates, uric acid and so on. The nitrogen source suitable for use includes ammonium sulfate, ammonium chloride, sodium nitrate, urea and other organic compounds, amino acids such as glutamic acid, nitrogen-containing natural products such as peptides, meat extract, soybean flour, uric acid and others. The inorganic materials used when it is desired to promote the growth of the microorganism and production of the enzyme include various kinds of phosphates, various kinds of sulfates such as magnesium sulfate, iron (II) sulfate and the like and various kinds of chlorides such as sodium chloride, potassium chloride and the like as well as zeolite, kaolin and so on. If necessary, the culture medium may be admixed with growth factors such as biotin, thiamine and the like.

Although the culturing of the microorganism can be performed either by the solid culture or by the liquid culture, the industrially most advantageous method is the liquid cultivation under aeration and agitation. The cultivation should be performed at a temperature in the range from 38° to 62° C. or, preferably, from 50° to 55° C. The pH of culture medium should desirably be neutral to weakly acidic. Though widely dependent on the cultivating conditions, the cultivation is usually continued for 6 to 20 hours and should be terminated when a substantial amount of the uricase can be detected in the medium or, preferably, when the amount of the uricase in the medium arrives maximum. The uricase of the invention produced by the microorganism is usually contained in the microbial cells but the uricase is also detected in the culture medium, especially, when culturing is at the last stage approaching the end.

The uricase contained in the cultured broth can be collected by any one or any combination of known methods without particular limitations. After completion of culturing, for example, the cultured broth is subjected to centrifugal separation to collect the microbial cells from which the uricase is extracted by a suitable means. The extract solution freed from insoluble matters and cell debris by centrifugation and the like is subjected to purification of the uricase contained therein by a combination of the methods including precipitation with an acid, precipitation with an organic solvent, salting-out, dialysis and various chromatographic methods such as ion exchange, gel filtration, hydrophobic chromatography and the like to give the uricase in a very high purity.

Following is a description of the properties of the uricase according to the invention. The sample used in the determination of the properties was the enzyme obtained in Example given below. The activity determination of the uricase was performed in most cases by the UV method described below utilizing the decrease in the ultraviolet absorption of uric acid at a wave length of 293 nm. The activity of the uricase is defined by taking a titer of the enzyme decomposing 1 μmole of uric acid for 1 minute under the conditions of determination given below as 1 U (unit). The activity in U/ml was calculated using the equation below:

Activity of uricase, U/ml =

$$\frac{\Delta OD \times (\text{overall volume of solution, ml}) \times (\text{times dilution})}{12.2 \times (\text{reation time, minutes}) \times (\text{volume of enzyme solution, ml})},$$

in which ΔOD is the decrease in the optical density at 293 nm during the reaction and 12.2 is the molecular extinction coefficient of uric acid given in cm²/micromole.

(1) Reaction catalyzed by the enzyme

The enzyme has an activity to catalyze the following reaction.

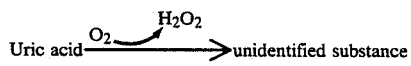

Uric acid $\xrightarrow{O_2 \quad H_2O_2}$ unidentified substance (2) Optimum pH (The effect of pH on activity)

Comparative test was undertaken using the uricase of the invention, a uricase derived from yeast (a product by Toyobo Co.) and a further uricase derived from Corynebacterium (a product by Seishin Seiyaku Co.). Each of the experiments for the reaction was performed by dissolving the enzyme in an amount corresponding to 10 mU/ml at 30° C. with a pH of 8.0 in a buffer solution having a varied pH as indicated in FIG. 1. The buffer solution was a 50 mM borate buffer solution containing 1 mM of EDTA·2Na and 0.001% of Triton X-100 and the final concentration of uric acid was 100 μM. The reaction was performed at 30° C. by agitating the solution in a cubette with a magnetic stirrer rod and measuring the decrease of UV absorption at 293 nm.

FIG. 1 shows the relative activity of each of the enzymes as a function of pH taking the activity thereof at the optimized pH as 100. As is shown in this figure, the enzyme of the invention exhibited a much higher activity than the other two enzymes even in a weakly acidic pH region and the activity thereof covered a wide range of pH from 5 to 10.

(3) The effect of pH on stability

Figure 2:
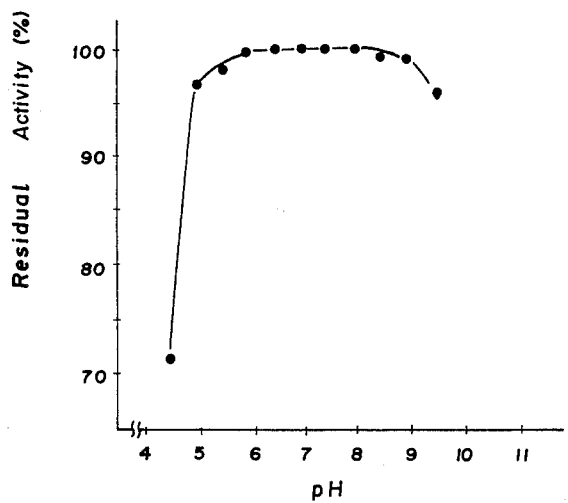

The enzyme of the invention was dissolved in a 50 mM phosphate buffer solution at a varied pH as indicated in FIG. 2 and containing 1 mM of EDTA·2Na and 0.001% Triton X-100 in a concentration of 200 mU/ml as determined at 30° C. with a pH of 8.0.

After standing as such for 15 days at 30° C., each of the enzyme solutions was diluted 20 times with a 50 mM borate buffer solution at a pH of 8.0 containing 1 mM of EDTA·2Na and 0.001% of Triton X-100 and then 100 μM of uric acid were added to the thus diluted solution having a pH of about 8.0 to effect the enzymatic reaction at 30° C. The activity of the enzyme was determined by the UV method and the results of the residual activity are shown in FIG. 2 for each value of pH taking the activity at the start of the test, i.e. without the treatment, as 100. The activity of the inventive enzyme was quite stable in the pH range between 5 and 9.

(4) Optimum temperature (The effect of temperature on activity)

Figure 3:
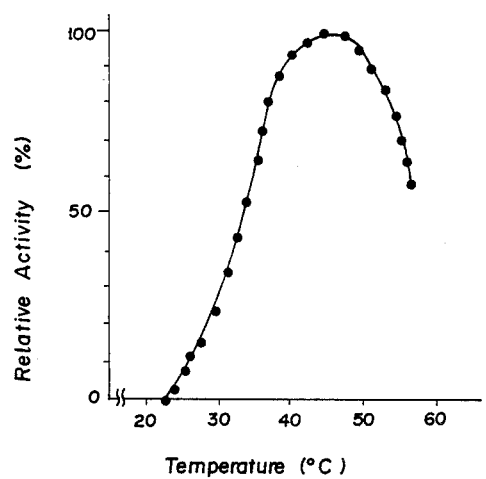

The enzyme of the invention was dissolved in a 50 mM borate buffer solution at a pH of 8.0 containing 1 mM of EDTA·2Na and 0.001% of Triton X-100 at a concentration of 10 mU/ml and the enzymatic reaction was performed with 100 μM or uric acid as the substrate at varied temperatures indicated in FIG. 3 for 6 minutes. The decrease of the uric acid concentration was determined by UV method. As is clear from FIG. 3 showing the relative activity of the enzyme at varied temperatures taking the largest value as 100, the enzyme of the invention had an optimum temperature at 45° to 50° C.

(5) The effect of temperature on stability

Figure 4:
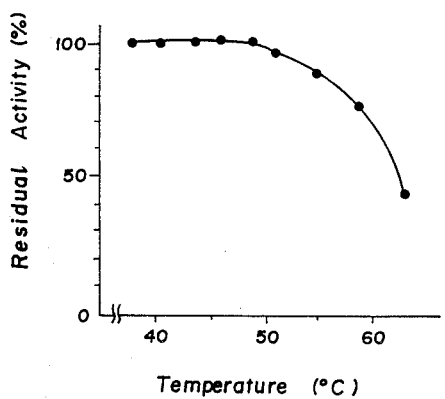

A solution of 8 mU of the inventive enzyme dissolved in 100 μl of a 50 mM borate buffer solution at a pH of 9.1 containing 1 mM of EDTA·2Na and 0.001% of Triton X-100 was kept standing for 10 minutes at a varied temperature indicated in FIG. 4 and then the residual activity of the enzyme was determined by the UV method at 30° C. with a pH of 8.0 using 100 μM of uric acid. The results are shown in FIG. 4 in which the relative activity is shown as a function of the temperature taking the activity of the fresh enzyme as 100. As is understood from the figure, no inactivation of the enzyme was observed after 10 minutes when the temperature was 50° C. or below fully keeping the initial activity.

(6) Tolerance against ionic surface active agents

Figure 5:
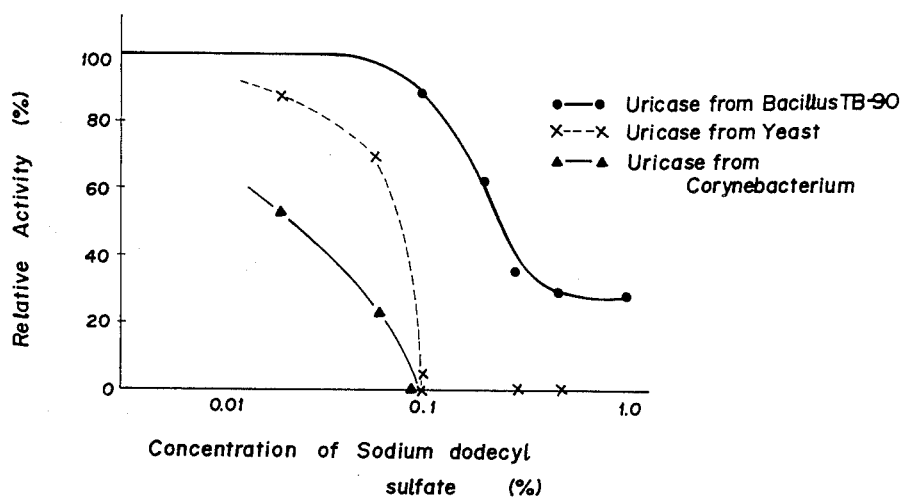

Comparative tests were undertaken using the same three kinds of the uricases as used in the above described test for the optimum pH by dissolving 20 mU of the enzyme in 2 ml of the solution for the UV photometric activity determination containing sodium dodecyl sulfate in a varied concentration to perform the enzymatic reaction on uric acid. The results are shown in FIG. 5 in which the activity of the enzyme is shown as a function of the concentration of the surface active agent taking the value obtained in the absence of the surface active agent as 100. As is understood from this figure, the enzyme of the invention was highly resistant against this protein-denaturating agent and the activity thereof was free from the inhibitive effect of sodium dodecyl sulfate up to a concentration of 0.08% while the other two commercially available uricases were susceptible to inhibition or denaturation.

(7) Substrate specificity

The activity of the inventive enzyme on several uric acid-related compounds was examined by means of the formation of hydrogen peroxide which was detected by the peroxidase method. Thus, 13 mU of the inventive enzyme were dissolved in 2 ml of the test solution for the peroxidase method described below and containing 200 μM of the substrate to determine the amount of hydrogen peroxide formed by the enzymatic reaction. The inventive enzyme, which was strictly specific on uric acid, was absolutely inactive on adenine, guanine, xanthine, hypoxanthine, theobromine and theophyline.

Following is a detail of the peroxidase method used for the detection of hydrogen peroxide.

Each of the substrate compounds in an amount corresponding to a concentration of 200 μM was dissolved in a 50 mM phosphate buffer solution at a pH of 6.5 containing 0.05% of Triton X-100, 490 μM of 4-aminoantipyrine, 5.3 mM of phenol and 6 U/ml of peroxidase, and 2.0 ml of the solution were admixed with 13 mU of the inventive enzyme to react on the tested substrate at 37° C. for 15 hours with formation of hydrogen peroxide. The amount of the hydrogen peroxide was determined by the increase in the absorption at a wave length of 500 nm as the $\lambda_{max}$ due to the coloring material formed in an amount proportional to the hydrogen peroxide.

(8) Molecular weight

The enzyme of the invention has a molecular weight of about 120,000 as determined by the gel filtration method.

As is mentioned before, an uricase is an enzyme useful for the quantitative determination of uric acid while quantitative determination of uric acid by use of a uricase can be performed in several different ways described below.

I. Uric acid is determined quantitatively by the determination of hydrogen peroxide produced by the enzymatic decomposition of uric acid by the aid of uricase, in which hydrogen peroxide can be determined by several different methods including:
(a) the uricase-peroxidase method as an enzymatic photometry in which hydrogen peroxide is reacted with 4-aminoantipyrine and phenol or its derivative thereof in the presence of peroxidase to form a coloring material in an amount proportional to the hydrogen peroxide followed by the determination of absorption;
(b) the uricase-catalase method as an enzymatic photometry in which hydrogen peroxide is reacted with an alcohol in the presence of catalase to form an aldehyde and the coloring material formed as a condensation product thereof with acetylacetone and ammonia is determined by the increase in the absorption; and
(c) the ultraviolet absorption method in which the above mentioned aldehyde as the reaction product by the aid of catalase is reacted with nicotinamide adenine dinucleotide of the reduced form (NADH) in the presence of alcohol dehydrogenase to form NAD and the decrease of the NADH is determined by the ultraviolet photometry.

II. Uric acid is quantitatively determined by the electrode method in which consumption of oxygen or formation of carbon dioxide is determined in the course of the decomposition of uric acid by uricase.

III. Uric acid is quantitatively determined by the absorption method utilizing the difference in the ultraviolet absorption due to the uric acid per se between the values before and after the reaction.

IV. The content of uric acid in the materials before and after the uricase treatment is determined by a chemical method for the quantitative determination of uric acid such as the phosphotungstic acid method.

Among the above described methods for the quantitative determination of uric acid, the most widely used is the uricaseperoxidase method. The pH of the reaction mixture in this case should be determined depending on the pH-activity characteristics of the uricase and it is essential that several factors should be taken into consideration including the stability of the coloring reagent, pH dependency of the sensitivity for the quantitative determination and the pHactivity characteristics of conjunctively used peroxidase which has the highest activity under weak acidity with a pH of 6.0 to 7.0.

Though dependent on the origin of the enzyme, uricases in general exhibit the highest activity under an alkaline condition with a pH of 8.0 to 9.0 and are absolutely inactive (see Japanese Patent Publication 56-43230) or only very weakly active (see Japanese Patent Kokai Koho 56-124381) under neutrality or under weak acidic pH region. Besides, an example is reported in Japanese Patent Kokai 56-81586 that a uricase of a specific type exhibits the highest activity in a weakly acidic pH region but the stability thereof under such a condition is extremely poor.

In view of the traditional procedure of the clinical analysis in which the reaction temperature in most cases is 37° C. for enzymatic reactions, on the other hand, the temperature dependency of the stability and activity of the enzyme is also an important factor to be taken into consideration. The uricase used for the quantitative determination of uric acid is also required to have a high activity so that the time taken for the reaction should be as short as possible and the amount of the enzyme used in the reaction should be as small as possible.

Following is a statement of the comparison between the uricase of the invention and a commercially available uricase derived from yeast (a product by Toyobo Co.) from the standpoint of using the enzyme for the quantitative determination of uric acid. In the comparative study, the above mentioned peroxidase method was utilized to examine the relationship between the amount of the used enzyme and the reaction time taken for the quantitative determination of uric acid while an inversely proportional relationship is generally held therebetween. The reaction conditions were substantially the same as described above including the kinds and amounts of the ingredients contained in the reaction mixture and the procedure for carrying out the reaction except that the concentration of uric acid was 37.2 μM.

The reaction time taken for completion of the reaction was given by the time from the start of the reaction to the moment when the absorption at 500 nm corresponding to the amount of the coloring material formed in proportion to the amount of the hydrogen peroxide became constant.

Figure 6:
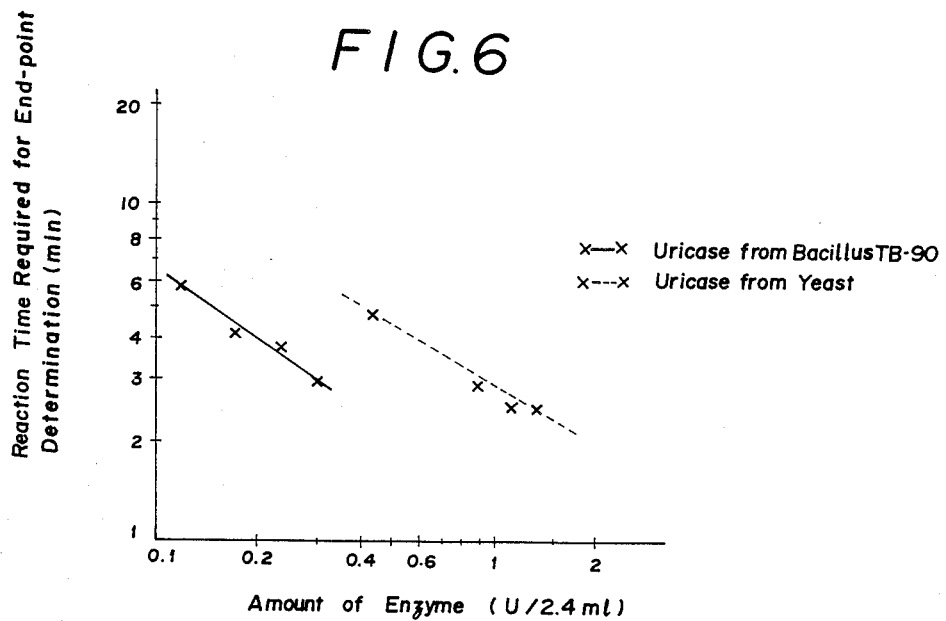
FIG. 6 shows the reaction time taken for the quantitative determination of uric acid by the peroxidase method as a function of the amount of the used enzyme.

As is understood from the results shown in FIG. 6, the activity of the inventive enzyme was so high that about the same results could be obtained by the use of the inventive enzyme in an amount of only 20% of units of the commercially available enzyme used for comparative purpose. The enzymatic activity in this case was calculated for the values of pH of 8.0 and 8.5, i.e. the optimum pHs, for the inventive and comparative enzymes, respectively, at 30° C. according to the UV method.

To summarize the advantages obtained by the inventive uricase, the enzyme has excellent stability owing to the thermophilic microorganism as the origin thereof and also has advantageous properties that the enzyme is active over a wide range of pH and highly resistant against surface active agents. Accordingly, the necessary amount of the enzyme can be greatly reduced in the quantitative determination of uric acid in comparison with conventional uricase derived from yeast. The quantitative determination of uric acid by use of the inventive enzyme can be performed by several different methods, of which the uricase-peroxidase method is preferable. The enzyme of the invention can be produced in a relatively short time with a high efficiency because it is a product of a thermophilic microorganism.

In the following, the novel uricase of the invention and the method for the preparation thereof are described in more detail by way of an example.

EXAMPLE

Into a large-size test tube were taken 10 ml of a seed culture medium prepared by dissolving in tap water 1 g/dl of glucose, 1 g/dl of yeast extract, 1 g/dl of peptone, 1 g/dl of potassium dihydrogenphosphate ($KH_2PO_4$), 1 g/dl of dipotassium hydrogenphosphate ($K_2HPO_4$) and 0.5 g/dl of magnesium sulfate ($MgSO_4 \cdot 7H_2O$) and, after sterilization at 121° C. for 15 minutes, the culture medium was inoculated with TB-90 as the seed. Culturing of the microorganism was performed by shaking the medium at 55° C. for 6 hours.

Thereafter, 30 ml of the thus obtained culture were added to 1.5 liters of a production culture medium in a jar fermenter of 5 liter capacity prepared by dissolving, in tap water, 3 g/dl of glucose, 1 g/dl of yeast extract, 0.5 g/dl of peptone, 4 g/dl of uric acid, 1 g/dl of potassium dihydrogenphosphate ($KH_2PO_4$), 0.5 g/dl of magnesium sulfate ($MgSO_4 \cdot 7H_2O$) and 0.5 g/dl of soybean oil and the cultivation was performed at 55° C. for 13 hours under agitation at a velocity of 300 rpm and aeration at a rate of 1 liter air/liter culture medium.

After completion of culturing, the bacterial cells collected by centrifugal separation were dispersed in 1 liter of a 0.1% aqueous solution of Triton X-100 and the aqueous dispersion was kept standing overnight at a temperature of 7° to 8° C. to effect extraction of the uricase into the aqueous phase followed by centrifugal separation of the dispersion to give a clear aqueous solution as the supernatant. The activity of uricase in this aqueous solution was 10 U/dl corresponding to an overall activity of 100 U in 1.0 liter of the aqueous solution as the supernatant.

The uricase-containing aqueous solution was acidified to have a pH of 4.1 by adding 3N acetic acid and kept standing at a temperature of 7° to 8° C. for 3 to 4 hours so that the uricase was precipitated. The uricase were recovered from the supernatant by decantation and then by centrifugal separation as precipitate.

The precipitates thus collected were dissolved in 100 ml of a 50 mM borate buffer solution having a pH of 8.0 and the solution was subjected to dialysis in a cellophane tube overnight at a temperature of 7° to 8° C. against 2 liters of a 50 mM phosphate buffer solution having a pH of 6.0. The thus dialyzed solution was passed through a column having an inner diameter of 2.5 cm and an effective length of 15 cm and filled with a weakly basic ion exchanger (DEAE-Biogel A, a product of Biorad Co.) in the Cl-form and equilibrated in advance with a 50 mM phosphate buffer solution having a pH of 6.0 so that the uricase was adsorbed on the carrier.

Thereafter, the carrier in the column was washed with 500 ml of a 50 mM phosphate buffer solution having a pH of 6.0 and subjected to elution of linear concentration gradient using 500 ml of the same buffer solution containing 0.4M of sodium chloride. The eluate was collected in fractions of each 10 ml volume. Fractions containing the uricase were combined and ammonium sulfate was added to the thus combined aqueous solution in a concentration of 60% saturation followed by collection of the precipitates in the solution by centrifugal separation.

The precipitates were dissolved in a small volume of a 50 mM phosphate buffer solution having a pH of 8.0 and the solution was charged to a column having an inner diameter of 2.5 cm and an effective length of 80 cm and filled with Sephadex G-200 (a product by Pharmacia Co.) equilibrated with the same buffer solution followed by elution with the same buffer solution. The eluate was collected in fractions of each 5 g weight and ammonium sulfate was added to the fractions containing the uricase and combined together in a concentration of 60% saturation to precipitate the uricase. The precipitates of the uricase collected by centrifugal separation were dissolved in a 50 mM borate buffer solution having a pH of 8.0 and the solution was subjected to dialysis overnight at a temperature of 7° to 8° C. in a cellophane tube as the dialysis membrane against 1 liter of the same buffer solution. The solution after completion of the dialysis was freeze-dried to give the uricase in a powdery form which had a specific activity of 3 U/mg protein. The yield of this uricase product was 41% based on the content thereof in the extract from the bacterial cells. The properties of this enzyme product were as described before.

What is claimed is:

1. A method for the preparation of a uricase capable of oxidatively decomposing uric acid and having activity therefor in a range of pH from 5 to 10 which comprises culturing a thermophilic microorganism designated Bacillus Sp TB-90 (FERM BP-795) in a nutrient culture medium for a time sufficient to produce the uricase and recovering the uricase.

* * * * *